(12) United States Patent
Evans

(10) Patent No.: US 6,298,496 B1
(45) Date of Patent: Oct. 9, 2001

(54) PROTECTIVE SURGICAL SOCK (FEET) PROTECTIVE SURGICAL COVERING FOR THE ARM, HAND

(76) Inventor: Idamae Francesina Evans, 9697 Brassie Way, Gaithersburg, MD (US) 20886

( * ) Notice: Subject to any disclaimer, the term of this patent is extended or adjusted under 35 U.S.C. 154(b) by 0 days.

(21) Appl. No.: 09/551,856

(22) Filed: Apr. 18, 2000

(51) Int. Cl.⁷ ..................................................... A41B 11/00
(52) U.S. Cl. .................... 2/239; 2/16; 2/59; 128/882; 602/3
(58) Field of Search ................. 2/16, 161.7, 59, 2/239, 240; 128/846, 882; 602/1, 3, 21, 23, 60, 62, 63, 65

(56) References Cited

U.S. PATENT DOCUMENTS

| | | | |
|---|---|---|---|
| 4,966,135 | * | 10/1990 | Renfrew ................................. 128/82 |
| 5,230,333 | * | 7/1993 | Yates et al. ........................... 128/382 |
| 5,497,513 | * | 3/1996 | Arabeyre et al. ........................ 2/240 |
| 5,575,013 | * | 11/1996 | Krack ........................................ 2/239 |
| 5,617,745 | * | 4/1997 | Della Corte et al. ................... 66/178 |
| 5,634,216 | * | 6/1997 | Wu ............................................ 2/239 |
| 5,658,354 | * | 8/1997 | Norvell ................................... 673/36 |
| 5,697,106 | * | 12/1997 | Baker et al. ............................. 2/239 |
| 5,720,712 | * | 2/1998 | Joy et al. ................................. 602/3 |
| 5,749,100 | * | 5/1998 | Rosenberg ................................ 2/239 |
| 5,830,237 | * | 11/1998 | Kania ..................................... 623/37 |

* cited by examiner

*Primary Examiner*—John J. Calvert
*Assistant Examiner*—Katherine Moran

(57) ABSTRACT

The intention of this current and improved invention relates to podiatry/orthopedic (entire foot/toe area, heel, ankle, lower and upper part of the leg) for providing the patient with a protective covering. The loose fit sock provides protection, flexibility, comfort, and adjustability during the rehabilitation/treatment process. In most cases (foot/toe area) after a procedure is done, an open surgical shoe is required to be worn by the patient. For the arm/hand area—when braces, casts, splints, fixtures, bandages and medicated patches (e.g.) are used after procedures, the components and variations are an asset. In addition, with both the foot/leg, and hand/arm coverings, the variations, components and materials are practical, safe, washable and reusable, and the manufacturing cost is minimal.

6 Claims, 12 Drawing Sheets

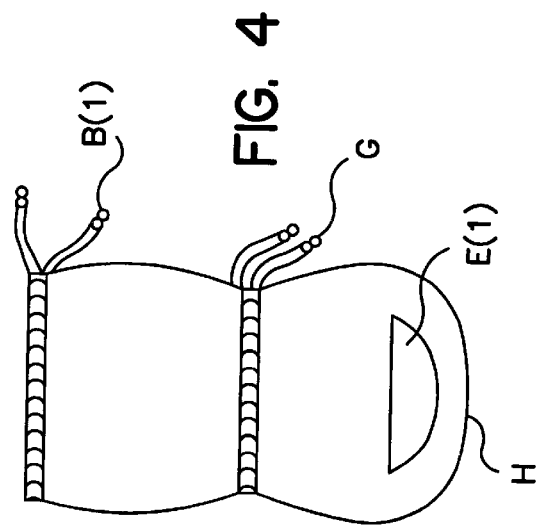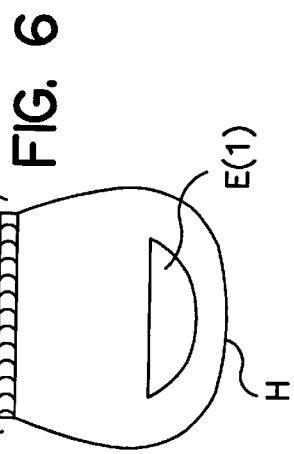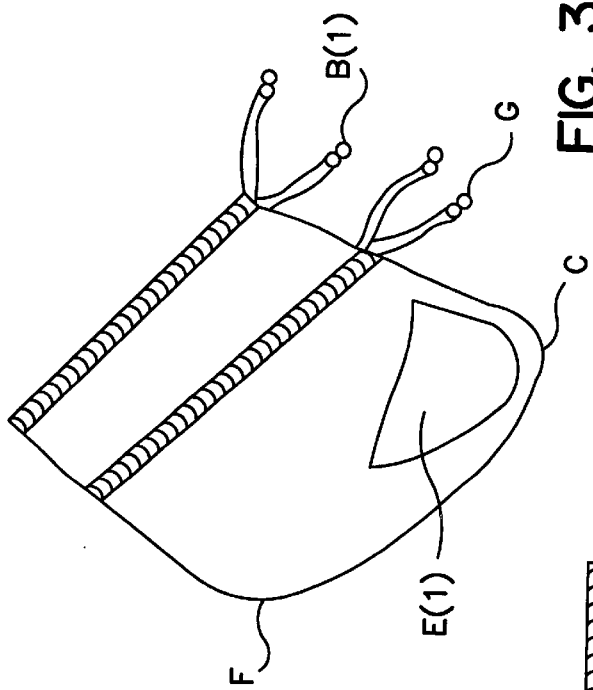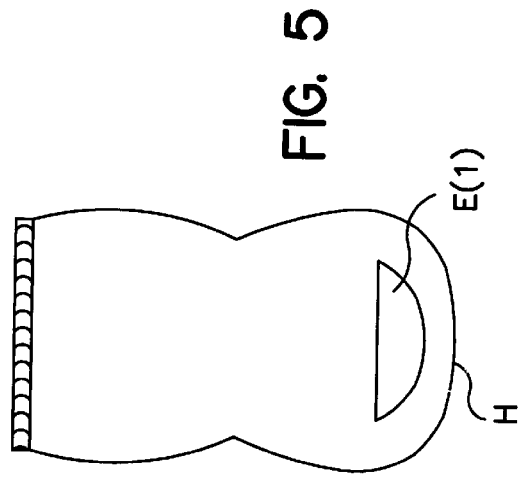

PROTECTIVE SURGICAL SOCK (FEET) PROTECTIVE SURGICAL COVERING FOR THE ARM, HAND

BACKGROUND OF THE INVENTION

This invention relates to protective sock used for the foot and entire toe area including the ankle, lower and upper part of the leg/knee. This protective Surgical Sock can be used in Podiatry/Orthopedic, Vascular and general related treatment/ rehabilitation after surgery, and will enhance the quality of the rehabilitation.

In the past there has been no known all season protective covering addressing the entire foot area and leg area. This covering is practical, safe, sanitary and reusable. In most instances during the course of treatment in the foot/toe area, a surgical shoe is worn during the healing/rehabilitation process. The surgical shoe in most instances is open. Surgery to the foot/toe area sometimes include pins in the toes, osteotomies (cutting) clamps, and stitches. This loose fitting sock with a variation of shapes, sizes, padding and materials will be workable and effective with the on going treatment process. The variation of the loose fit shape-sock will be referred to as (a) sock-like and (j) Pear-Sock-with varying components.

In reference to the lower and upper leg area, the protective sock is adaptable and adjustable where casts, bandages and dressings are used, and the toe and heel area are most times left unprotected.

In the past there has been no known all seasonal protective covering addressing the arm/hand area. This current and improved invention for the forelimb (arm), the carpus (wrist), the metacarpus (palm proper) and the digits (the four fingers and the thumb) addresses fractures, surgery, and other diseases of the arm and hand. This protective covering will provide the patient with the same protection as the Protective Surgical Sock for the foot, lower and upper leg area. In most instances the digits are exposed. The flexibility, variations in materials, sizes and components will be workable and effective in the on going rehabilitation/treatment process. This covering is safe, practical and sanitary where casts, bandages, splints, braces, external fixtures, dressings (e.g.) may be used. This Tub-shape-Mit will be referred to as (y). This Tub-shape Mit is easily maintained, hand washable and reusable.

BRIEF SUMMARY OF THE INVENTION

The object of this invention is to provide the patient with adequate/suitable protection. The variations in sizes, shapes, designs and materials will be an asset. Most designs will be suitable for the open surgical shoe and will adequately cover casts, pins, clamps, bandages, tapes and other dressings. The patient will have the flexibility of movement as much as existing injuries will allow, but the Protective Surgical Sock will be an asset. Most of the sock-like coverings will have extra padding.

Maintenance of this sock-like covering is relatively easy since it can be hand washed and reused. Protective Tub-shape Mit (y) will be an asset. This design will be suitable for the arm/hand area for adequately covering casts, braces, fixtures, splints, bandages, tapes and other dressings. The motivation and object of this current invention will be clarified in the following drawings.

BRIEF DESCRIPTION OF THE DRAWINGS

FIG. 3 Outline of the Protective Surgical Sock This version covers the lower half of the leg and entire foot (toes) area.

FIG. 4 Pear Shape-Sock like (j) addresses the loose fit practical for bandages, Casts, tapes, pins (e.g.) foot (toes) lower and upper leg area.

FIG. 5 Pear Shape-Sock-like (j) addresses the loose fit practical for bandages, casts, tapes, pins (e.g.) foot (toes) lower and upper leg area.

FIGS. 1–18 address some variations and components with the patient in mind for comfort, flexibility and protection from the elements. (FOOT)

| | | |
|---|---|---|
| Top tie draw strings | foot | b (1) |
| Top tie draw strings | hand | b (2) |
| Semi-rounded toe | foot | c |
| Lining/insulation | foot | d (1) |
| Lining/insulation | hand arm | d (2) |
| Fore Foot padding | foot | e (1) |
| Heel padding | foot | e (2) |
| Ball of foot padding | foot | e (3) |
| Heel | foot | f |
| Tie drawstrings | foot | g |
| Rounded toe | foot | h |
| Tie strings (upper sock) | (lateral) foot | I (1) |
| Tie draw strings (left arm) | (lateral) | I (2) |
| Tie draw strings (right arm) | (lateral) | I (3) |
| Pear Shape-Sock-like | foot | j |
| Tie drawstrings (middle) right and left side | foot | k |
| All around ties | foot | l |
| Back zipper (posterior) | foot | m |
| Front zipper (anterior) | foot | n |
| Zipper left side | foot | o (1) |
| Zipper left side | arm | o (2) |
| Zipper right side | foot | p (1) |
| Zipper right side | arm | p (2) |
| All around zipper | foot | q |
| Zipper Fore foot | foot | r |
| Side zippers left and right | foot | s |
| Buttons left side | foot | t (1) |
| Buttons left side | arm | t (2) |
| Buttons right side | foot | u (1) |
| Buttons right side | arm | (u) 2 |
| Snaps./hooks left side | hand arm | u (3) |
| Snaps/hooks right side | hand arm | u (4) |
| Elastic (top) | arm | v |
| Diagonal (toe shapes) | foot | w |
| Forearm/hand | hand arm | x |
| Tub-shape-Mit | hand arm | y |
| Digits | fingers thumb | z |

DETAILED DESCRIPTION OF THE INVENTION

Protective Surgical Sock . . . Shape (a) and Shape (j)

Figure 1:
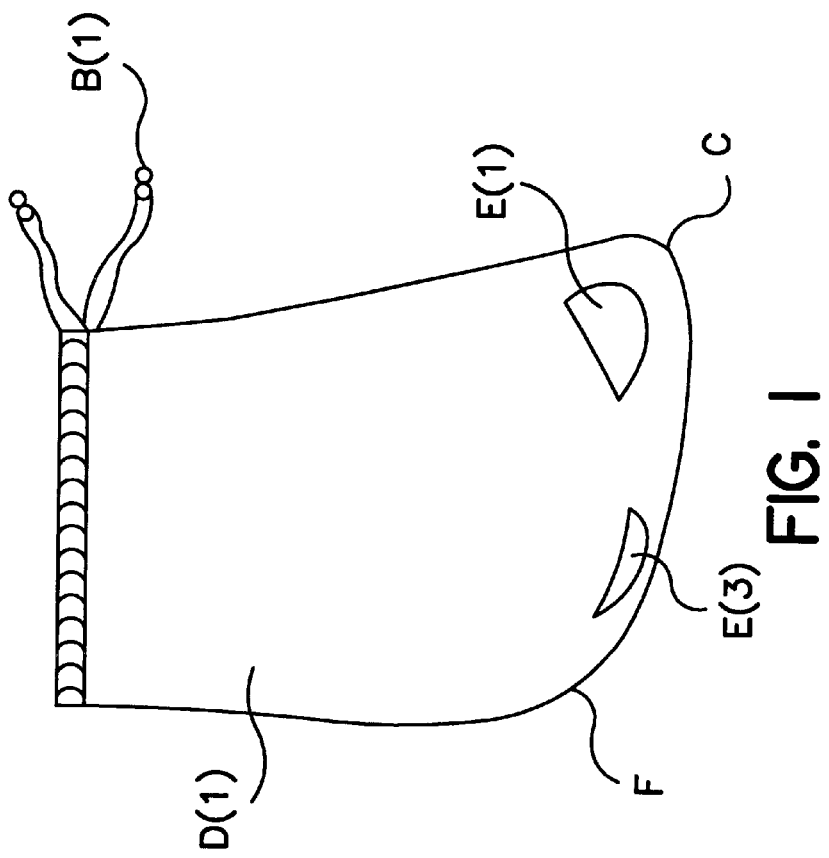
FIG. 1 Outline of the Protective Surgical Sock (a) with possible examples of materials to be used in promoting this current invention in relation to injury, rehabilitation, seasonal/environmental conditions.

FIG. 1. Sock (a) Top left. Padding and Insulation: Variety of fabrics cotton, terry cloth, sweat cloth, plastic coated (e.g.) for use.

| Top left | |
| --- | --- |
| Top tie draw strings | b (1) |
| Semi-rounded toe | c |
| Lining/Insulation | d (1) |
| Fore foot padding | e (1) |
| Ball of foot padding | e (3) |
| Heel | f |

Figure 2:
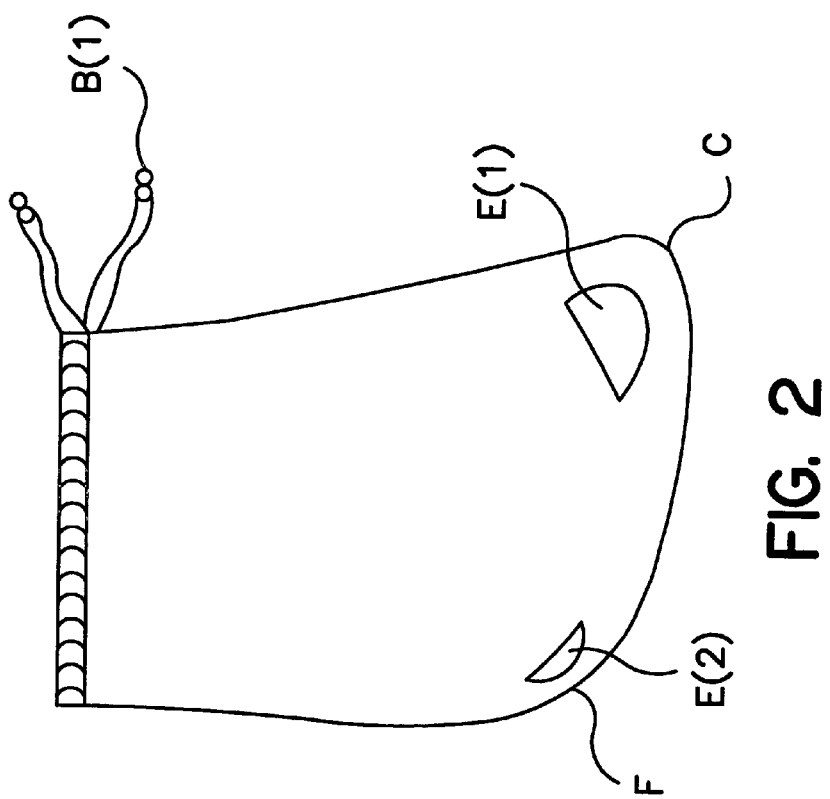
FIG. 2 Outline of the Protective Surgical Sock (a) addresses the loose Fit, practical for bandages, casts, tapes, pins (e.g.) foot (toes) lower and upper leg area.

FIG. 2. Sock (a) Top-right Out-line Sock (a) loose fitting, practical for bandages, casts, pins (e.g.)

| Top right | |
| --- | --- |
| Top tie draw strings | b (1) |
| Semi-rounded toe | c |
| Fore foot padding | e (1) |
| Heel | f |

TIE DRAW STRINGS

FIG. 3. Sock (a) Short

| Top left | |
| --- | --- |
| Top tie drawstrings | b (1) |
| Semi-rounded toe | c |
| Fore foot padding | e (1) |
| Heel | f |
| Tie draw strings (middle) | g |

FIG. 4 (j)

| Top right | |
| --- | --- |
| Top tie drawstrings | b (1) |
| Fore foot padding | e (1) |
| Tie draw strings (middle) | g |
| Rounded toe | h |

FIG. 5. Pear-shape-sock (j)

| Bottom left Loose fitting, practical for bandages, casts, tapes, pins (e.g.) | |
| --- | --- |
| Fore foot padding | e (1) |
| Rounded toe | h |

FIG. 6. Pear-shape-sock (j)

| Bottom right | |
| --- | --- |
| Fore foot padding | e (1) |
| Rounded toe | h |
| Left and right side tie strings - (upper sock) | l |

Figure 7:
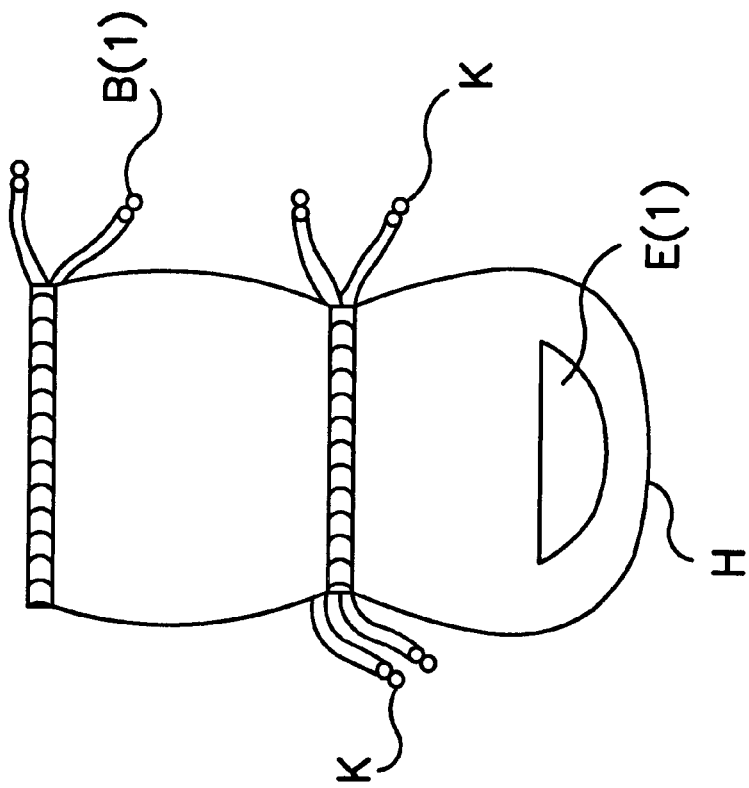

FIG. 7. VERSION 7. Pear-shape-sock (j)

| Top left | |
| --- | --- |
| Top tie drawstrings | b (1) |
| Fore foot padding | e (1) |
| Rounded toe | h |
| Tie draw strings (middle) right and left side | k |

Figure 8:
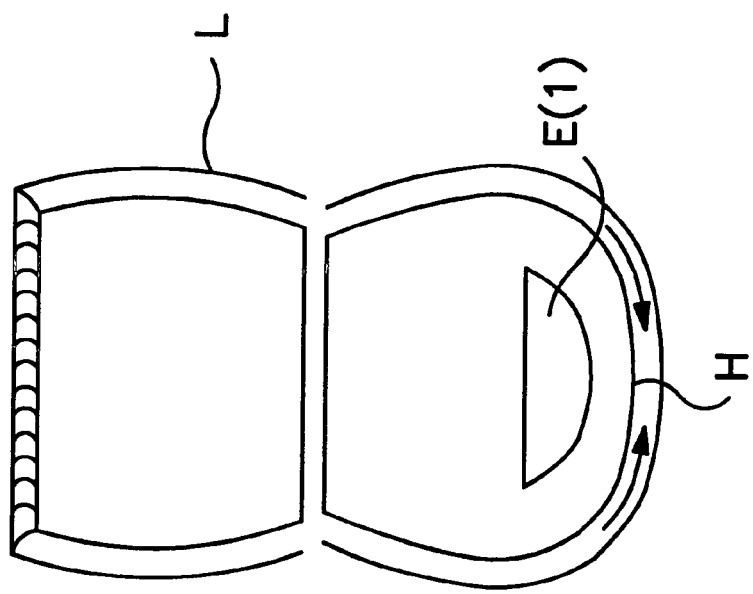

FIG. 8. VERSION 8. Pear-shape-sock (j)

| Top right | |
| --- | --- |
| Fore foot padding | e (1) |
| Rounded toe | h |
| All around ties | l |
| ZIPPERS | |

FIG. 9. Sock (a)

| Top left | |
| --- | --- |
| Top tie drawstrings | b (1) |
| Semi-rounded toe | c |
| Fore foot padding | e (1) |
| Heel | f |
| Back zipper (posterior) | m |

FIG. 10. Sock (a)

| Top right | |
| --- | --- |
| Top tie drawstrings | b (1) |
| Semi-rounded toe | c |
| Fore foot padding | e (1) |
| Heel | f |
| Front zipper (anterior) | n |

FIG. 11. Sock (a)

| Top left | |
| --- | --- |
| Semi-rounded toe | c |
| Fore foot padding | e (1) |
| Heel | f |
| Zipper left side | o (1) |

FIG. 12. Sock (a)

| Top right | |
|---|---|
| Semi-rounded toe | c |
| Fore foot padding | e (1) |
| Heel | f |
| Zipper right side | p (1) |

FIG. 13. Sock (a)

| (MIDDLE) | |
|---|---|
| Semi-rounded toe | c |
| Fore foot padding | e (1) |
| Heel | f |
| All around zipper | q |

Figure 14:
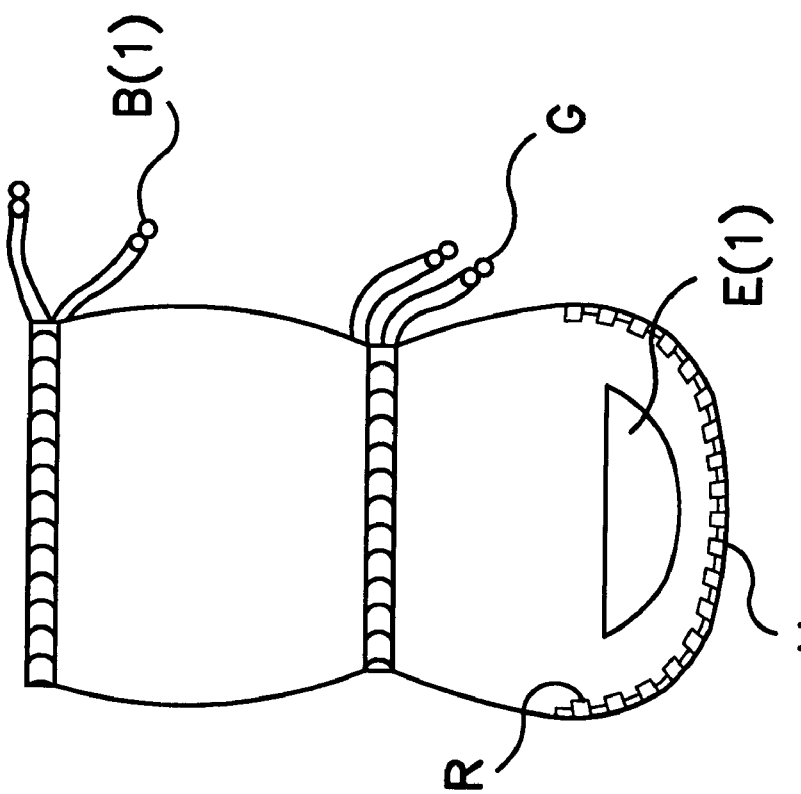

FIG. 14. Pear-shape-sock (j)

| Top left | |
|---|---|
| Top tie drawstrings | b (1) |
| Fore foot padding | e (1) |
| Tie draw strings (middle) | g |
| Rounded toe | h |
| Zipper (anterior toe area) | r |

Figure 15:
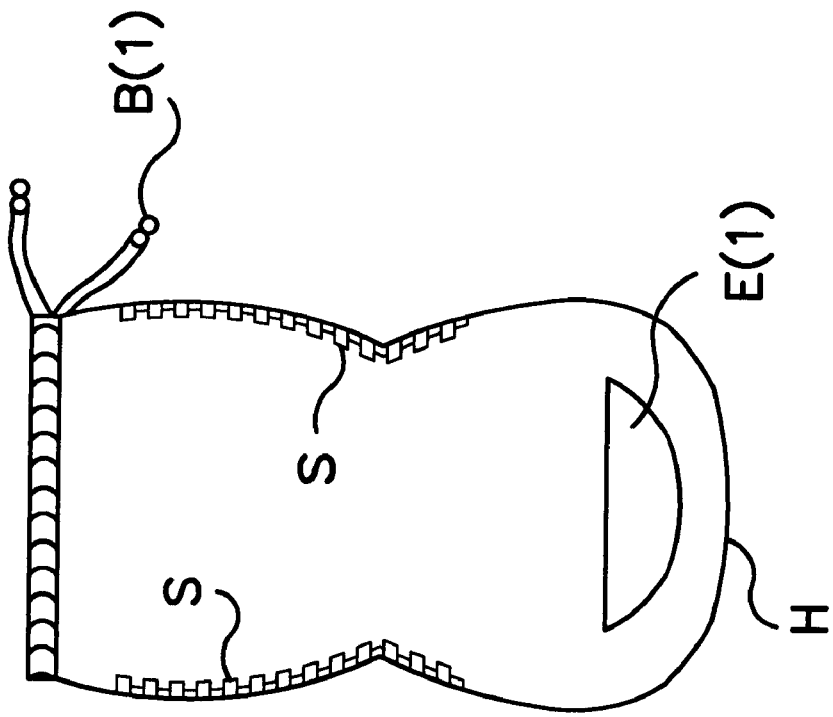

FIG. 15. Pear-shape-sock (j)

| Top right | |
|---|---|
| Top tie drawstrings | b (1) |
| Fore foot padding | e (1) |
| Rounded toe | h |
| Side zippers (left and right) | s |

FIG. 16. Sock (a)

| Top left | |
|---|---|
| Semi-rounded toe | c |
| Fore foot padding | e (1) |
| Heel | f |
| Buttons left side | t (1) |

FIG. 17. Sock (a)

| Top right | |
|---|---|
| Semi-rounded toe | c |
| Fore foot padding | e (1) |
| Heel | f |
| Buttons right side | u (1) |

FIG. 18.

| Left side | |
|---|---|
| Semi-rounded toe | c |
| Middle | |
| Rounded toe | h |
| Right side | |
| Diagonal sides right and left | w |
| Rounded toe | h |

FIGS. 19–26 Tub-shape-Mit for the arm/hand: a variation that will address features and components that protect and allow the patient the flexibility of movement as much as existing injuries will allow during the rehabilitation/treatment process. Materials and components are washable, very easy to care for, and reusable. This protective covering will be conducive to changing seasonal and environmental conditions. The Tub-shape-Mit (y), variations and components are practical for braces, splints, casts, fixtures, bandages and medicated patches (e.g.).

HAND/ARM

Figure 19:
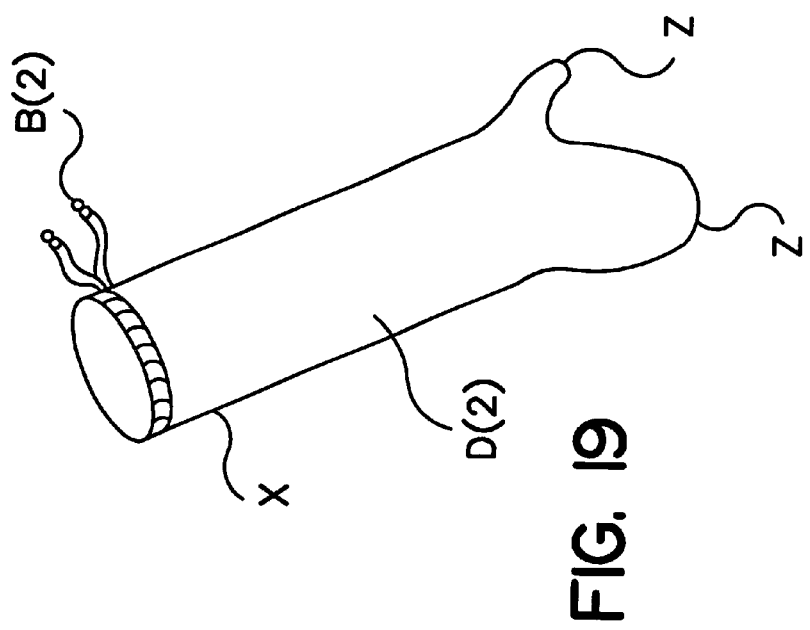

FIG. 19. Tub-shape-Mit (y)

| Top left<br>Padding and Insulation: Variety of fabrics<br>Cotton, terry cloth, sweat cloth, plastic coated (e.g.) for use. | |
|---|---|
| Top tie drawstrings | b (2) |
| Lining/insulation | d (2) |
| Fore arm | x |
| Digits/thumb | z |

Figure 20:
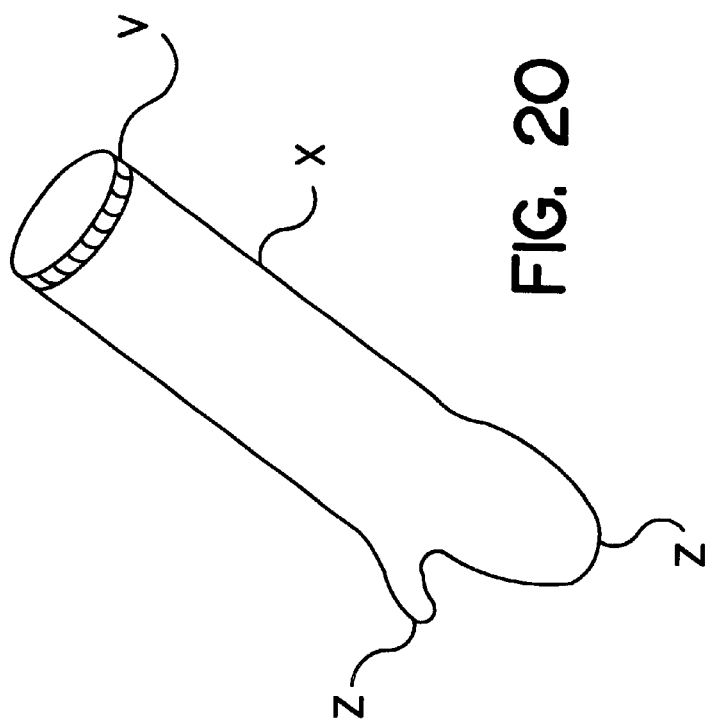
FIGS. 19–26 address a Tub-shape-Mit (y), with components and the patient in mind for comfort, flexibility, and an element protector. (ARM/HAND)

FIG. 20. Tub-shape-Mit (y)

| Top-right<br>Out-line of (y-Mit) practical design for braces,<br>bandages, splints, casts and fixtures (e.g.) | |
|---|---|
| Top fore arm (elastic) | v |
| fore arm | x |
| digits/thumb | z |

Figure 21:
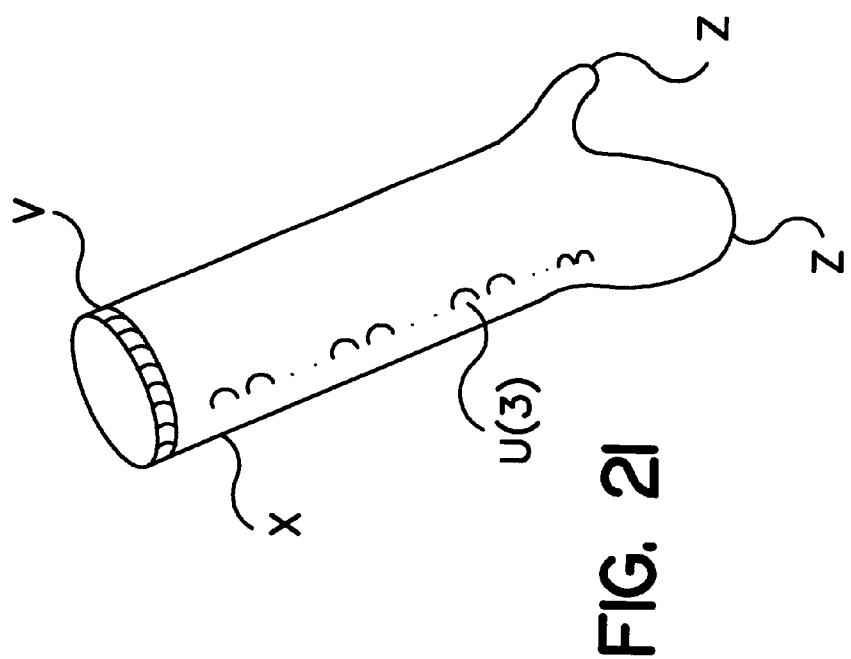

FIG. 21. Tub-shape-Mit (y)

| Top left | |
|---|---|
| Snaps/hooks (left fore arm) | u (3) |
| Top left (fore arm) elastic | v |
| Fore arm | x |
| Digits/thumb | z |

Figure 22:
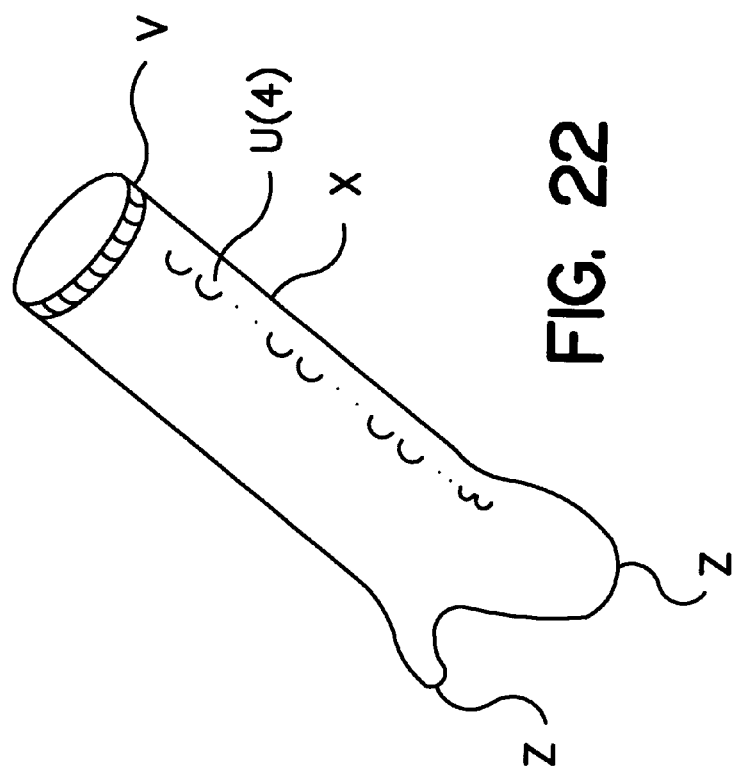

FIG. 22. Tub-shape-Mit (y)

| Top right | |
| --- | --- |
| Snaps/hooks right (fore arm) | u (4) |
| Top right (fore arm) elastic | v |
| Digits/thumb | z |

Figure 23:
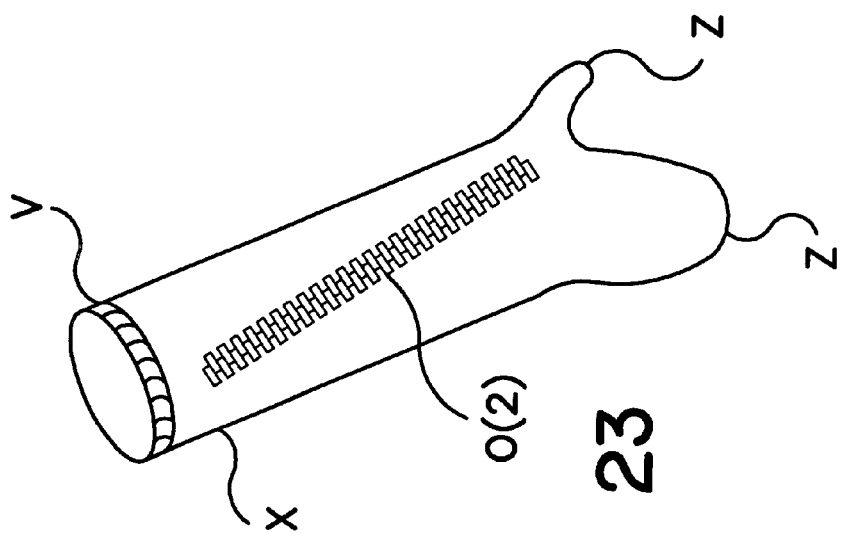

FIG. 23. Tub-shape-Mit (y)

| Top left | |
| --- | --- |
| Left arm (lateral zipper) | o (2) |
| Top left (fore arm) elastic | v |
| fore arm | x |
| Digits/thumb | z |

Figure 24:
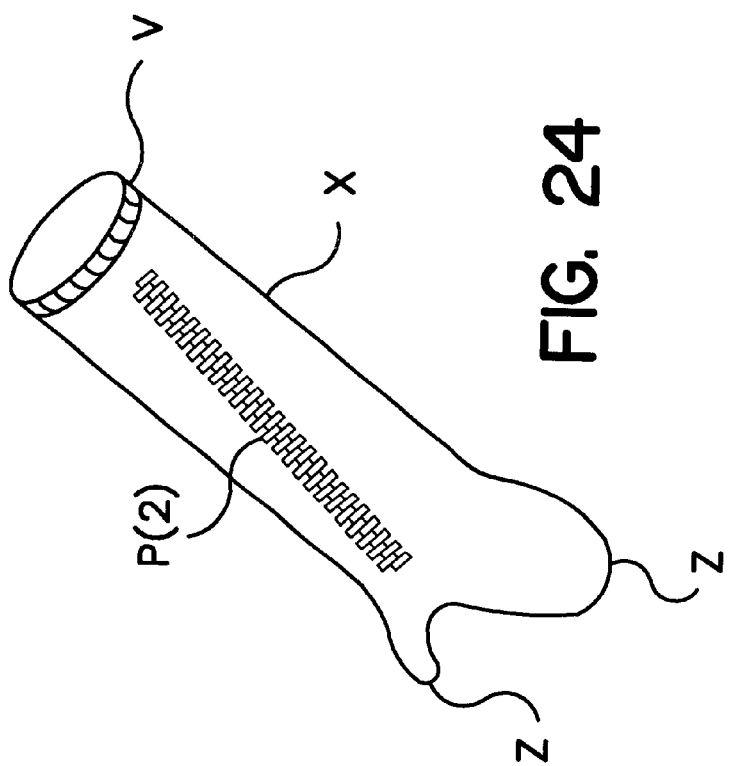

FIG. 24. Tub-shape-Mit (y)

| Top right | |
| --- | --- |
| Right arm (lateral zipper) | p (2) |
| Top left (fore arm) elastic | v |
| fore arm | x |
| Digits/thumb | z |

Figure 25:
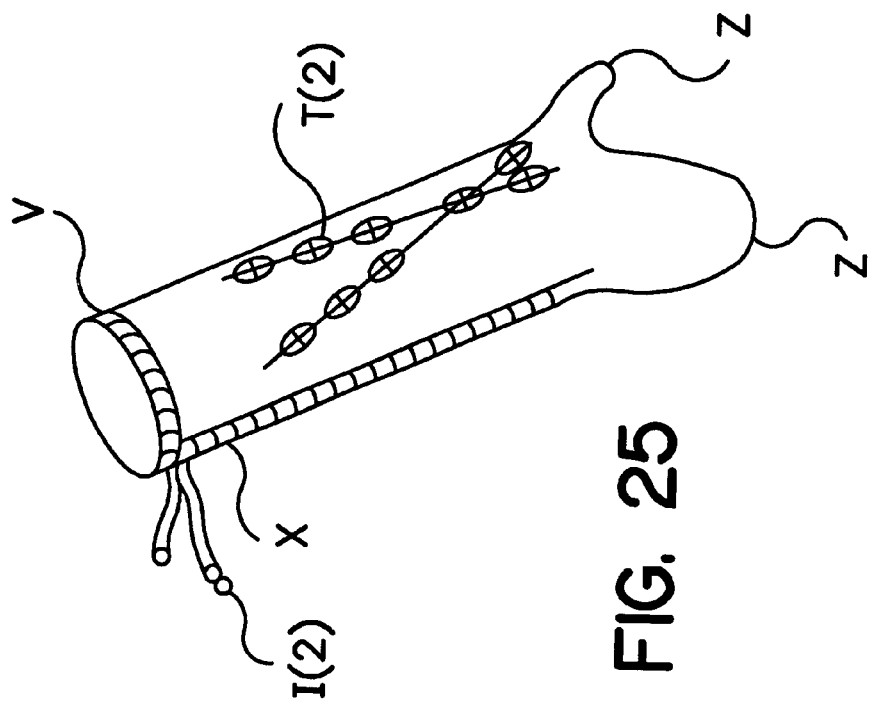

FIG. 25. Tub-shape-Mit (y)

| Top left | |
| --- | --- |
| Tie drawstrings left lateral (fore arm) | I (2) |
| Buttons left lateral (fore arm) | t (2) |
| Top left (fore arm) elastic | v |
| Fore arm | x |
| Digits/thumb | z |

Figure 26:
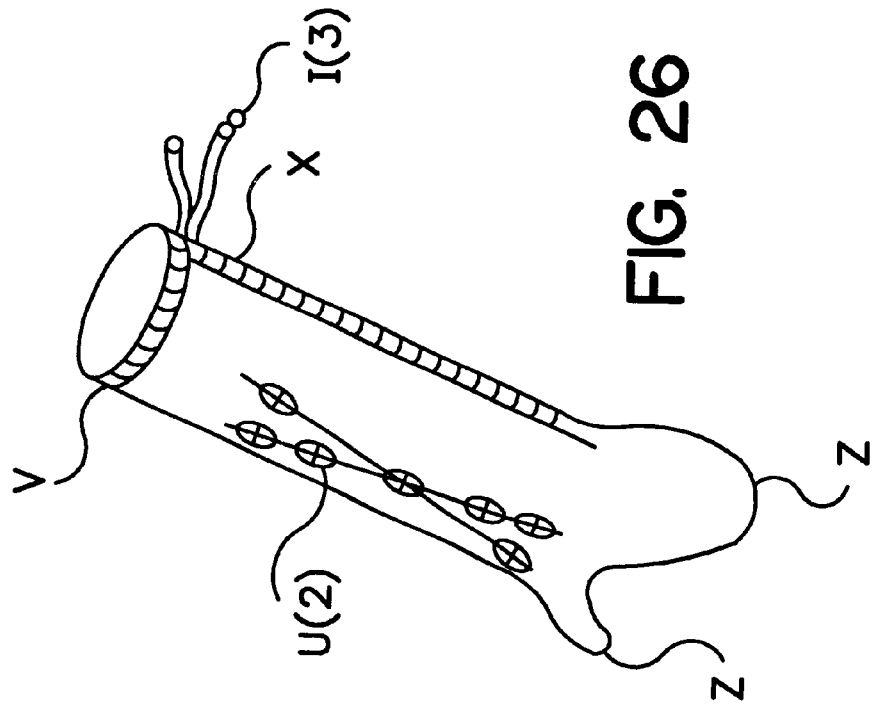

FIG. 26. Tub-shape-Mit (y)

| Top right | |
| --- | --- |
| Tie draw strings lateral (fore arm) | I (3) |
| Buttons right lateral (fore arm) | u (2) |
| Top right (fore arm) elastic | v |
| Fore arm | x |
| Digits/thumb | z |

STRUCTURAL FEATURES

The sock is made from a variety of fabrics including cotton, terry cloth, sweat cloth, muslin, plastic coating (e.g.), Strings, buttons, and zippers, are used for closure, secureness, adjustability, and flexibility.

STRUCTURAL FEATURES AND COMPONENTS: SOCK (a)

FIG. 1. Sock (a)

The Protective Surgical Sock is machine stitched from the top, with a turned down machine stitched hem, tie draw strings (b-1) incorporated and extended through hemmed opening for closure, secureness, and adjustability for inserting the foot, lower and upper leg into the opening without atraumatics to the patient. The machine stitching continues from the hemmed top to one side of the sock to the other side of the sock.

The sock includes Lining/Insulation (d-1) inside of the protective Surgical Sock (a). Terry cloth material may be used on the inside for added protection in the fore foot area, semi-rounded toe (c), and ball of foot padding (e-3). The terry cloth material is machine stitched to the plantar on the inside of the protective covering, and at the heel (f), for added protection on the inside of the sock (a) completely covering the inside of the Protective Surgical Sock (a).

Terry cloth material may also be sewn to the interior surface of the sock at the heel area (f) for reinforcement.

FIG. 3 shows a shorter sock with forefoot padding and tie drawstrings at top and middle positions for adjustably securing the sock.

Figure 9:
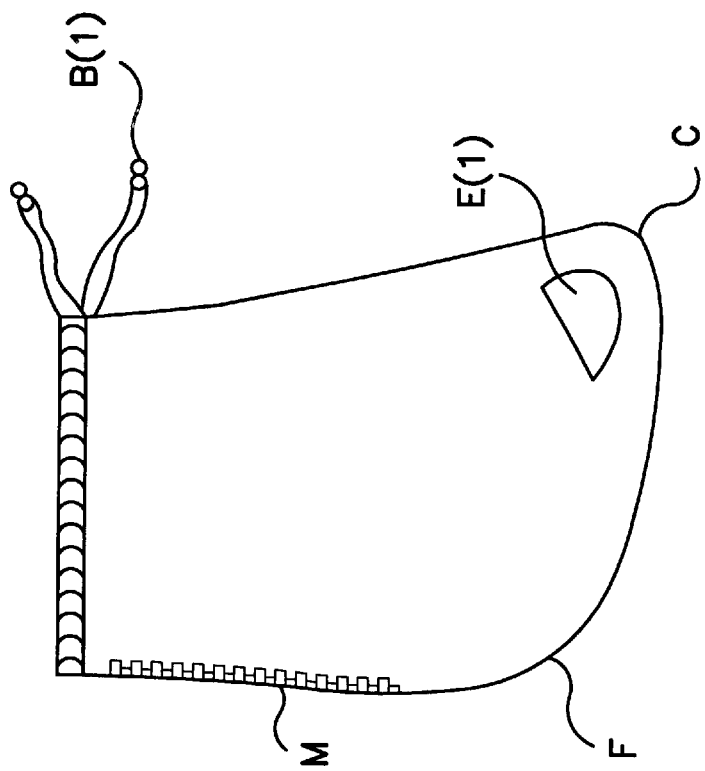

FIG. 9 shows an embodiment with a zipper along a side seam and a tie drawstring at the top.

Figure 10:
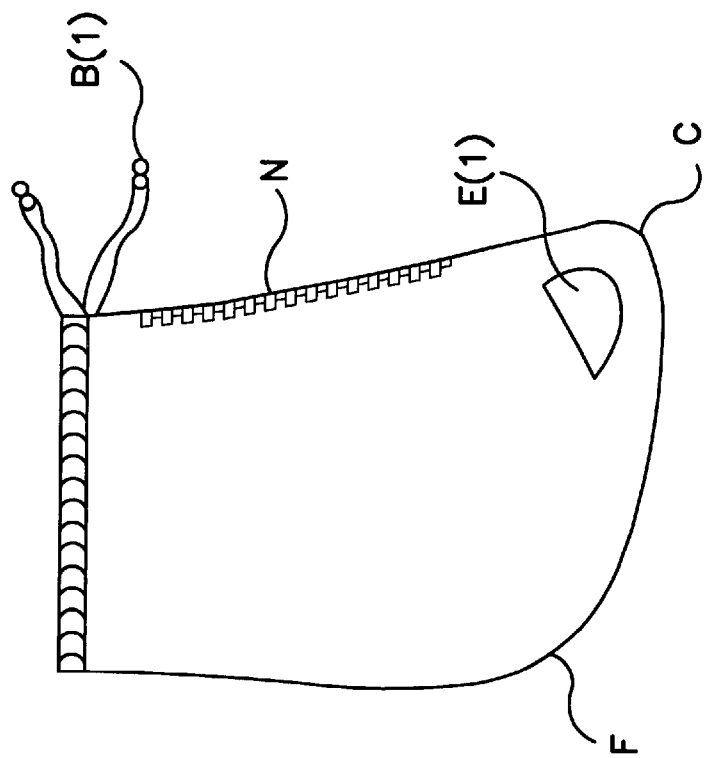

FIG. 10 shows an embodiment with a zipper along a left side seam.

Figure 11:
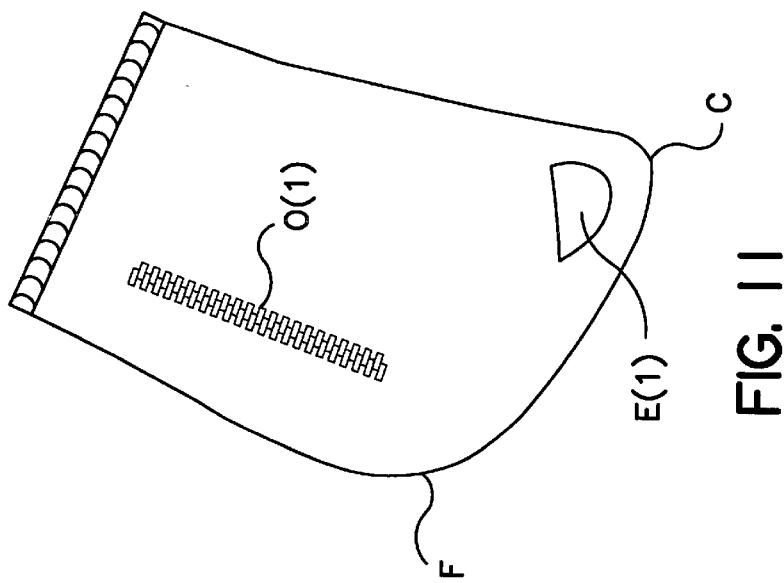

FIG. 11 shows a sock with a zipper located adjacent to the heel portion (f) with fore foot padding (e-1)

Figure 12:
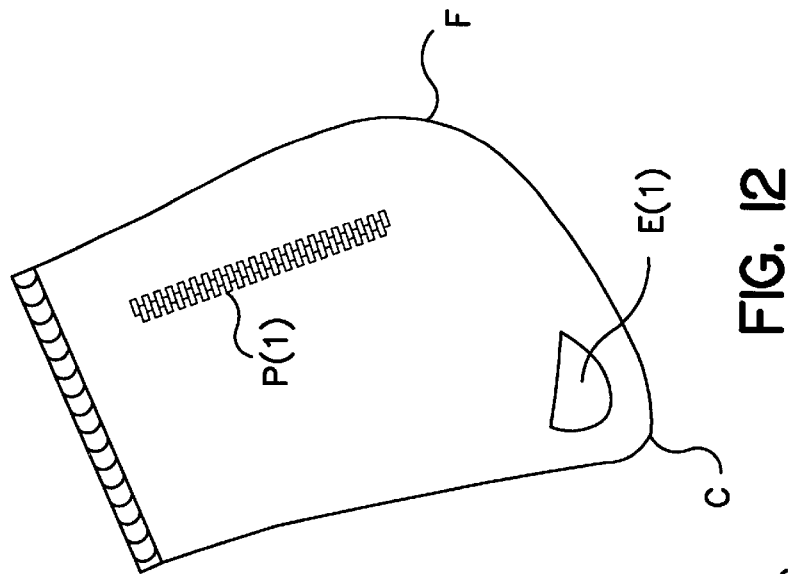

FIG. 12 shows a sock with the zipper located on the opposite side of the sock.

Figure 13:
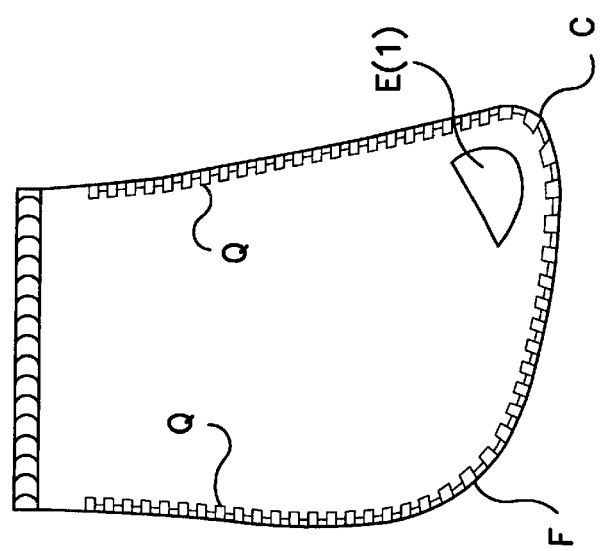

FIG. 13 shows a sock with a zipper (q) extending about the outer periphery of the sock.

Figure 16:
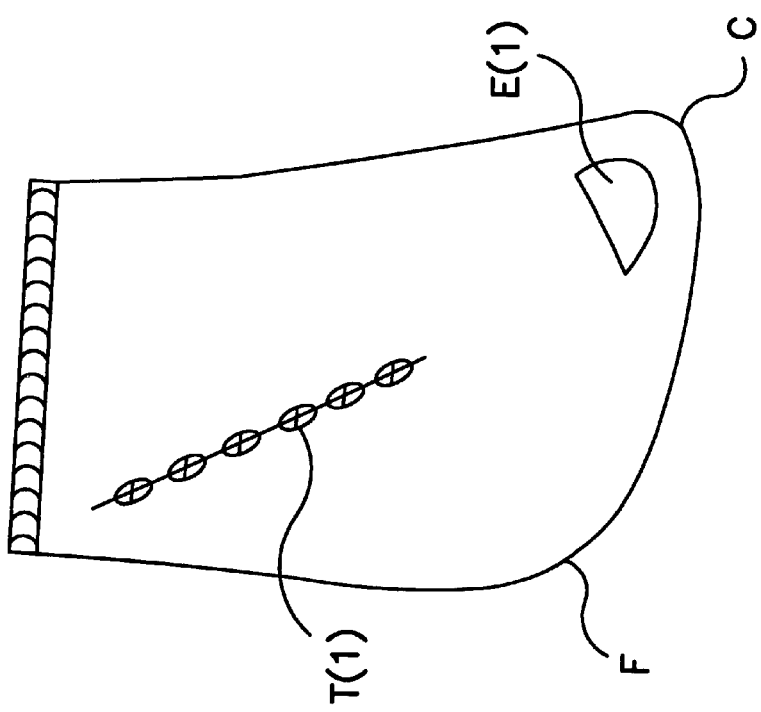

FIG. 16 shows the sock with buttons extending a long a top portion, with complementary buttonholes (not shown)

Figure 17:
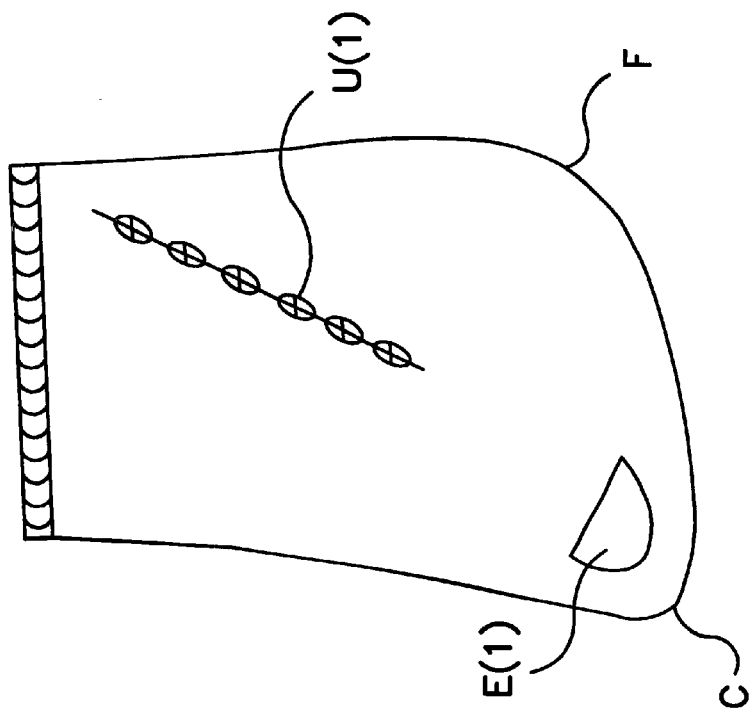

FIG. 17 shows the sock with buttons extending along the bottom sock portion.

FIG. 4.

A Pear-shape-sock (j) is machine stitched from the top wide opening, with a turned down machine stitched hem, and tie draw strings extending through the hemmed opening for closure, secureness, adjustability. Fore foot padding (e-1) is machine stitched at the anterior of the Protective Surgical Sock (j), with terry cloth material (not visible.

FIG. 5.

A Pear-shape-sock (j) is machine stitched from the top wide opening, with a turned down machine stitched hem, and machine stitching continues from turned down machine-stitched hem, from one top side to the other top side of said sock (laterally). Fore foot padding (e-1) is machine stitched at the anterior of the Protective Surgical Sock (j), with terry cloth material covering the toes on the inside of the material for added protection.

Heel padding (e-2) of terry cloth material is machine stitched on the inside of the (f) area for reinforcement.

FIG. 6. Pear-shape-sock (j)

Protective Surgical Sock (j) has fore foot padding E(j) and drawstrings extending vertically along opposing sides of the sock for securing the sock on the foot.

FIG. 7. Pear-shape-sock (j)

Protective Surgical Sock (j) has fore foot padding E(1) with a variation of the draw strings.

FIG. 8. Pear-shape-sock-like (j)

Protective Surgical Sock (j) shows another embodiment with tie drawstrings.

FIG. 14. Pear-Shape-Sock (j)

Protective Surgical Sock (j) has an opening extending from one side to the other at the toe end of the sock and a zipper closure for selectively opening and closing the toe area of the sock for exposing a wearer's toe area. The sock also includes fore foot padding and tie draw strings at the middle and upper end of the sock.

FIG. 15. Pear-shape-sock (j)

Protective Surgical Sock (j) has yet another embodiment with zippers extending vertically along the sides of the sock and a tie draw string at the top.

Figure 18:
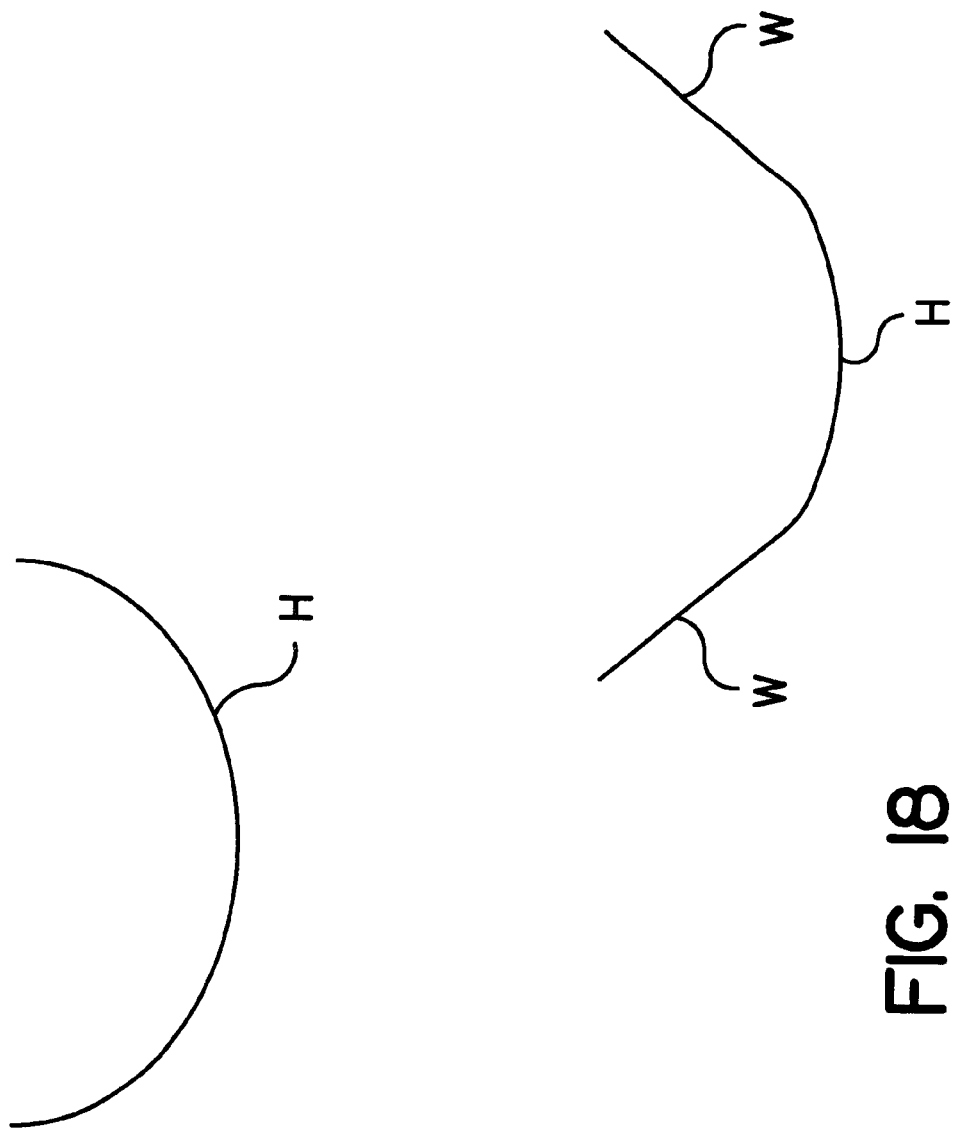

FIG. 18 shows different shapes of the toe portion of the sock.
PROTECTIVE COVERING-ARM/HAND TUB-SHAPE MIT (Y)
FIG. 19.

Tub-shape-mit (y) is a mitten with a thumb enclosure a tie drawstrings at an upper end.
FIG. 20.

Tub-shape-mit (y) is a mitten with a thumb enclosure and elastic at an upper end for securing the covering around an arm.
FIG. 21.

Tub-shape-mit (y) is a mitten with an elongated sleeve adapted to extend midway up a wearer's arm and including an opening along the length of the sleeve with snaps for closing the opening. The sleeve has an elastic upper end.
FIG. 22.

Tub-shape-mit (y) is the mitten of FIG. 21 with the vertical opening on the opposite side of the sleeve.
FIG. 23.

Tub-shape-mit (y) is a mitten with a zipper closure.
FIG. 24.

Tub-shape-mit (y) is the mitten of FIG. 23 with the zipper on the opposite side of the sleeve.
FIG. 25.

Tub-shape-mit (y) is a mitten with tie drawstrings at an upper end and buttons with complementary buttonholes for closing an opening extending vertically along the length of the sleeve.

FIG. 26 is the mitten of FIG. 25 with the opening along an opposite side of the sleeve portion

What is claimed is:

1. A sock for providing cushioning comfort to a foot comprising:

a stocking arranged to be loosely positioned over the foot, the stocking having a top, bottom, two side portions, a distal end, and a cushioned, quilted portion positioned over a toe area of the top of the stocking, a first closure positioned in a semi-circular configuration extending from one side to the other at a toe end of the stocking, wherein the toe area of a wearer is readily accessible, and a second closure at a distal end.

2. A sock according to claim 1, wherein the distal end is positioned to cover an ankle and lower leg area of a wearer.

3. A sock according to claim 1, wherein the stocking is made from a material selected from the group consisting of:

terry cloth, cotton, and plastic-coated material.

4. A sock according to claim 1, wherein the first closure is a zipper.

5. A sock according to claim 1, wherein the first closure is a button and buttonhole.

6. A sock according to claim 1, wherein the second closure is a drawstring located at each side portion for adjustably securing the distal end around a leg portion of a wearer.

* * * * *